(12) United States Patent
Zhou et al.

(10) Patent No.: US 10,475,528 B2
(45) Date of Patent: Nov. 12, 2019

(54) METHODS FOR MODELING AND ANALYSIS OF INTERFACE BETWEEN POINT PATTERNS

(75) Inventors: Weiqiang Zhou, ZhuHai (CN); Hong Yan, Hong Kong (CN)

(73) Assignee: CITY UNIVERSITY OF HONG KONG, Kowloon (HK)

( * ) Notice: Subject to any disclaimer, the term of this patent is extended or adjusted under 35 U.S.C. 154(b) by 820 days.

(21) Appl. No.: 13/188,598

(22) Filed: Jul. 22, 2011

(65) Prior Publication Data

US 2013/0024175 A1    Jan. 24, 2013

(51) Int. Cl.
| | |
|---|---|
| *G01N 33/48* | (2006.01) |
| *G06G 7/48* | (2006.01) |
| *G16C 20/50* | (2019.01) |
| *G16B 15/00* | (2019.01) |

(52) U.S. Cl.
CPC ............. *G16C 20/50* (2019.02); *G16B 15/00* (2019.02)

(58) Field of Classification Search
None
See application file for complete search history.

(56) References Cited

PUBLICATIONS

Cazals et al. "Revisiting the Voronoi description of protein—protein interfaces" (Protein Science, vol. 15 (2006) pp. 2082-2092).*
Liang et al. "Analytical Shape Computation of Macromolecules: I. Molecular Area and Volume Through Alpha Shape" (Proteins: Structure, Function and Genetics, vol. 22 (1998) pp. 1-17).*
Peters et al. "The Automatic Search for Ligand Binding Sites in Proteins of Known Three-dimensional Structure Using only Geometric Criteria" (J. Mol. Biol., vol. 256 (1996) 201-213.*
Zhou et al. "A Discriminatory Function for Prediction of Protein-DNA Interactions based on Alpha Shape Modeling", Bioinformatics, vol. 26 (2010) pp. 2541-2548.*

\* cited by examiner

*Primary Examiner* — Anna Skibinsky
(74) *Attorney, Agent, or Firm* — Amin, Turocy & Watson, LLP

(57) ABSTRACT

Methods, systems, and articles of manufacture are described that facilitate computation of a model of an interface between two molecules and analyzing characteristics of the interface. The complex of the two molecules can be modeled, and location of the atoms on the surface can be determined. One of the two molecules can be similarly modeled, and the location of the atoms on the surface can be determined. An interface model utilizing atoms that are located in the same place on the complex and the molecule can be calculated. Properties of the interface can be utilized to analyze the interaction between the two molecules.

22 Claims, 12 Drawing Sheets

METHODS FOR MODELING AND ANALYSIS OF INTERFACE BETWEEN POINT PATTERNS

TECHNICAL FIELD

This disclosure generally relates to modeling and analyzing an interface structure between sets of points in three-dimensional (3D) space.

BACKGROUND

Interactions between different biomolecules, such as proteins, deoxyribonucleic acid (DNA), and ligands, are essential for many biological processes. Protein-DNA interaction plays an important role in DNA replication, transcription and nucleosome remodeling. Protein-ligand interaction can be an important feature in drug design.

A drug molecule can be a ligand to a certain protein. As a ligand, the drug molecule can interact with the protein or dock to the protein, preventing the protein from functioning properly, which can be essential in stopping a disease causing process. Determining a protein for which a drug molecule can act as a ligand to is important to the design of drugs that can stop a disease causing process. Traditionally, biological experiments have been used to determine whether a drug molecule is a ligand that will interact with or dock to a given protein. However, these biological experiments are both costly and time consuming.

The foregoing description is merely intended to provide an overview of some of the problems with traditional methods for determining whether a ligand will interact with or dock to a given protein, and is not intended to be exhaustive. Problems with the state of the art and corresponding benefits of some of the various non-limiting embodiments may become further apparent upon review of the following detailed description.

SUMMARY

The following presents a simplified summary of the various embodiments in order to provide a basic understanding of some aspects described herein. This summary is not an extensive overview of the disclosed subject matter. It is intended to neither identify key or critical elements of the disclosed subject matter nor delineate the scope of the subject embodiments. Its sole purpose is to present some concepts of the disclosed subject matter in a simplified form as a prelude to the more detailed description that is presented later.

Various non-limiting embodiments are directed to a method for computing the interface between two molecules. For example, the interface can be between a protein and a ligand or a protein and a DNA molecule. The method can provide an improvement in the field of drug design and drug delivery.

The method can include developing a first model based on the complex. The first step can include receiving a first input of positions of two or more atoms in a complex of the two molecules. Based on the first input, a Delaunay triangulation can be constructed, and an alpha shape can be constructed based on the Delaunay triangulation.

The method can also include developing a second model based on a molecule of the complex. The second stem can include receiving a second input of positions of two or more atoms in the molecule of the complex. Based on the second input, a second Delaunay triangulation can be constructed, and a second alpha shape can be constructed based on the second Delaunay triangulation. The method can include constructing the interface between the molecules in the complex as part of the second alpha shape. From the interface pattern, features can be computed and a classifier can be built for the prediction of molecular interactions (e.g., protein-DNA interactions, protein-ligand interactions, or the like).

Also described herein are systems and articles of manufacture that facilitate execution of embodiments of the method for computing the interface. The methods, systems and articles of manufacturer described herein can be utilized, for example, to facilitate new drugs and/or new proteins. The methods, systems, and articles of manufacture described herein can construct interfaces illustrating protein-ligand docking, protein-DNA interfaces, or the like. However, the methods, systems, and articles of manufacture are not limited to interactions between biomolecules. Instead, the methods, systems, and articles of manufacture can be utilized for the modeling and analysis of the interface between two point patterns of any type.

The following description and the annexed drawings set forth in detail certain illustrative aspects of the disclosed subject matter. These aspects are indicative, however, of but a few of the various ways in which the principles of the various embodiments may be employed. The disclosed subject matter is intended to include all such aspects and their equivalents. Other advantages and distinctive features of the disclosed subject matter will become apparent from the following detailed description of the various embodiments when considered in conjunction with the drawings.

DETAILED DESCRIPTION

Various aspects relate to methods for modeling and analyzing an interface surface between sets of points in a three-dimensional (3D) space. The method can be applied to any patterns containing two or more sets of points in three or more dimensional space. According to an embodiment, atoms in a biomolecule can be represented in points with positions in 3D space. The positions can be taken as input to the method, and the method can compute an interface surface and its features, characteristics, or the like. The features or characteristics can be utilized to design pattern classifiers that can facilitate prediction of biomolecular interactions.

Figure 1:
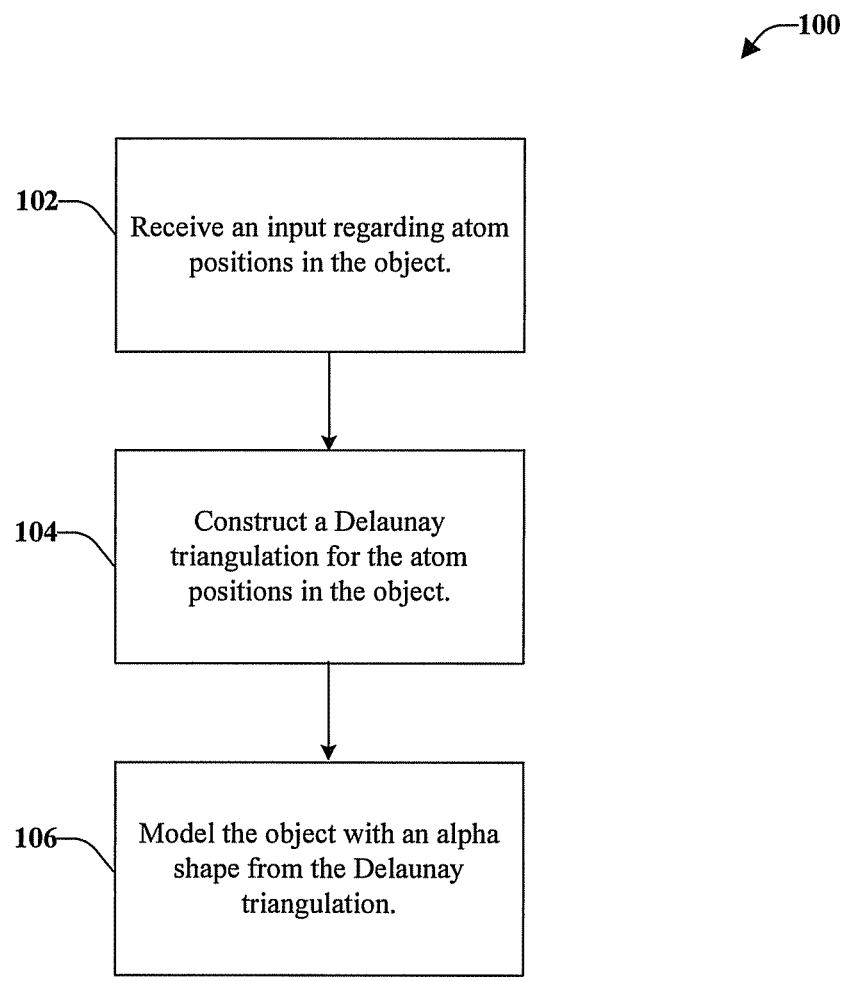
FIG. 1 is a schematic process flow diagram of a method for modeling an object.

Referring now to FIG. 1, illustrated is a schematic process flow diagram of a method 100 for modeling an object. For simplicity of explanation, the method 100 can be an algorithm that is depicted and described as a series of acts. The acts can be one or more instructions stored in a memory that can be executed by a computer processor. The acts of method 100 can be stored on an article of manufacture to facilitate transporting and transferring method 100 to a computer. According to an embodiment, an article of manufacture can be a computer program accessible from any computer-readable device, carrier, or media. For example, the computer-readable medium can be any non-transitory computer-readable storage medium.

The object can be anything that can be represented by points with positions in 3D space. One such object is a biomolecule, such as a protein, a DNA molecule, a ligand, or the like. The object can also be a complex between biomolecules that can form between a protein and a protein, a protein and a DNA or RNA, a protein and a ligand, or a DNA and a ligand. By way of example, a protein-DNA complex is described with regard to method 100.

At element 102, an input regarding atom positions in the object can be received. The input can include information as to the position of two or more atoms. Using the example of a protein-DNA complex, the input can include information as to the position of two or more atoms of the protein-DNA complex in a 3D space. The information as to the position of two or more atoms of the protein-DNA complex can be obtained through X-ray crystallography. The information can also be extracted from the Protein Data Bank (PDB).

Figure 2:
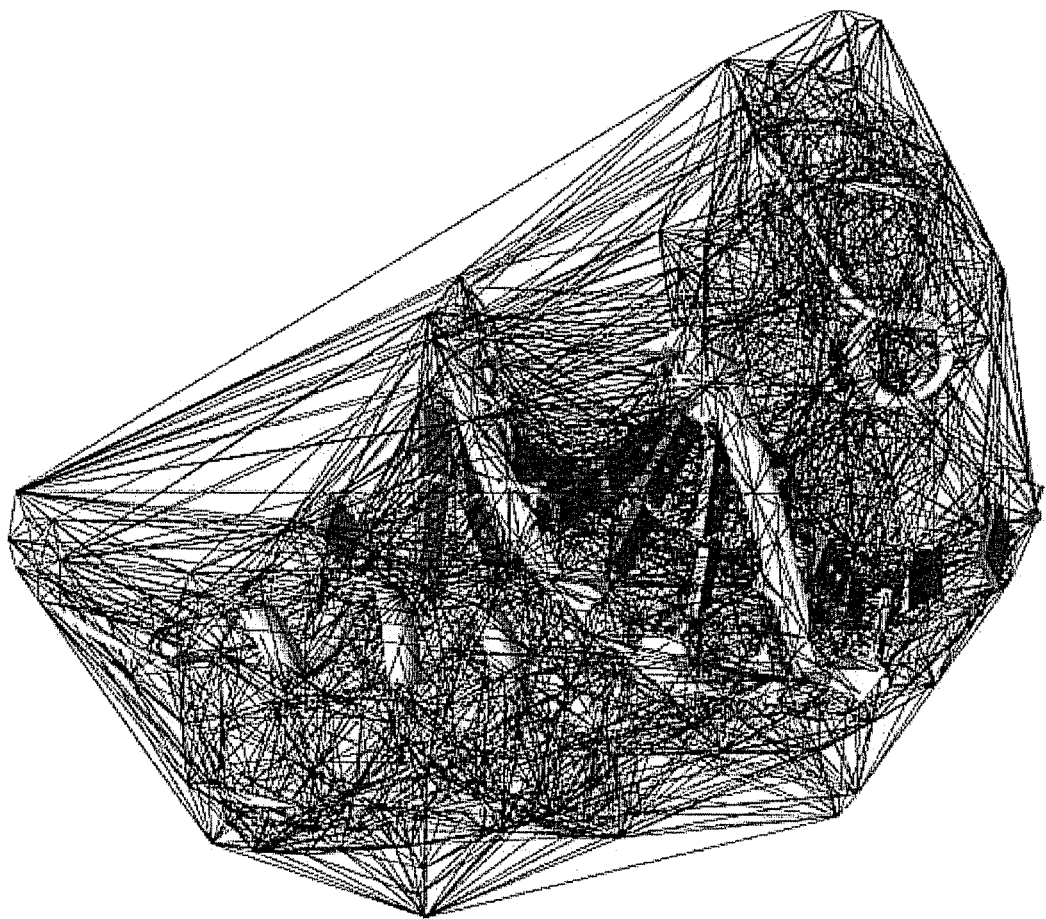
FIG. 2 illustrates an example of the edges of a Delaunay triangulation for a protein-DNA complex.

At element 104, a Delaunay triangulation can be constructed for points representing the atom positions of the input received at element 102. The Delaunay triangulation for a set of P points in a plane is a triangulation DT(P) such that no point in P is inside the circum circle of any triangle of DT(P). Delaunay triangulations maximize the minimum angle of all the angles of the triangles in the triangulation. The Delaunay triangulation can be extended to three dimensions by considering circumscribed spheres. In fact, the Delaunay triangulation of a set of points in d-dimensional spaces is the projection of the points of a convex hull onto a (d+1)-dimensional paraboloid. An example of the edges of the Delaunay triangulation based on atom positions in a protein-DNA complex can be found in FIG. 2. As shown in FIG. 2, the Delaunay triangulation is a unique partition of 3D space in nonoverlapping tetrahedrons.

Figure 3:
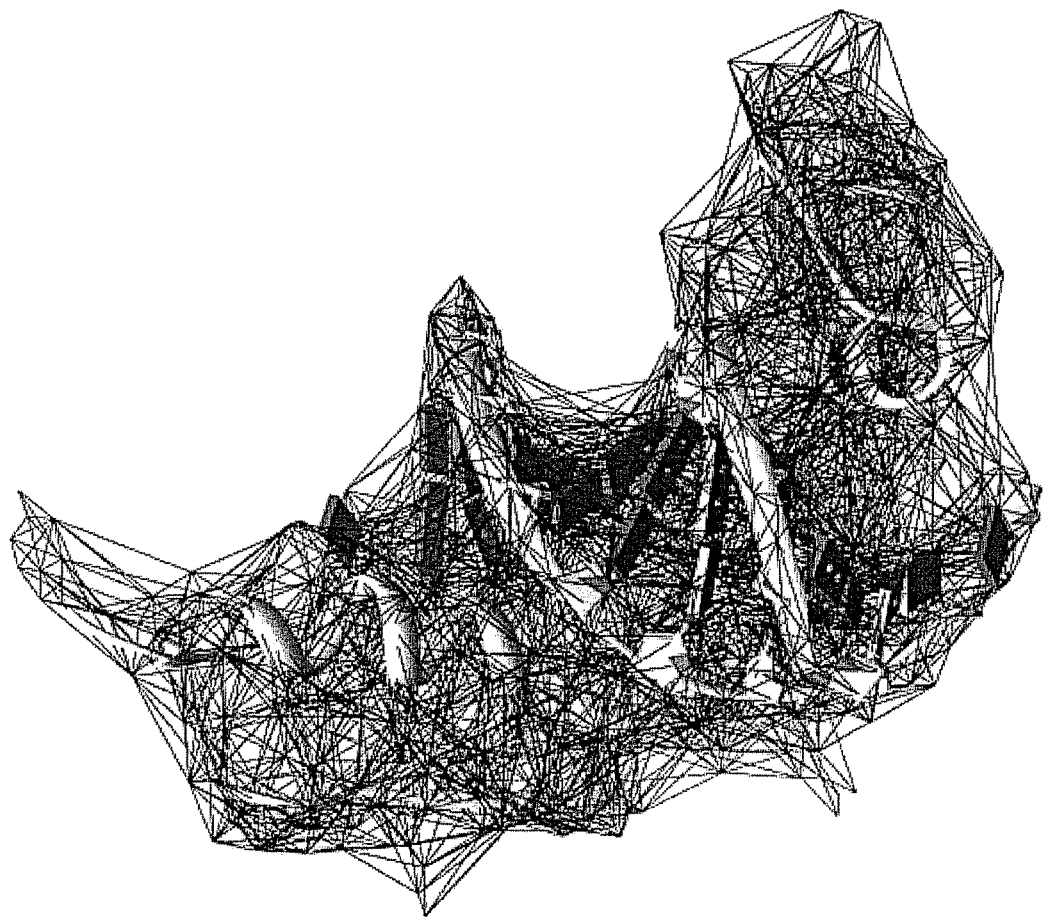
FIG. 3 illustrates an example of the edges of an alpha shape obtained from the Delaunay triangulation of FIG. 2.

At element 106, an alpha shape can be constructed from the Delaunay triangulation constructed at element 104. The edges of the Delaunay triangulation constricted at element 104, as shown in FIG. 2, cannot efficiently represent the surface of the complex; however, the edges of the Delaunay triangulation constricted at element 104 provide all of the edges needed to construct an alpha shape at element 106. As illustrated in FIG. 3, an alpha shape is developed by trimming the edges of the Delaunay triangulation. The alpha shape is a subset of the tetrahedrons in the Delaunay triangulation, which is a generalization of the convex hail of the point set of atom positions. The value of a controls the preciseness of the model.

More specifically, the alpha complex is defined as the set of points S that is a sub-complex of the Delaunay triangulation. For a given value of α, the alpha complex includes all the simplexes in the Delaunay triangulation that have an empty circumsphere with a squared radius equal to, or smaller than, α. Here 'empty' means that the open sphere does not include any points of S. The alpha shape is then simply the domain covered by the simplexes of the alpha complex.

Figure 4:
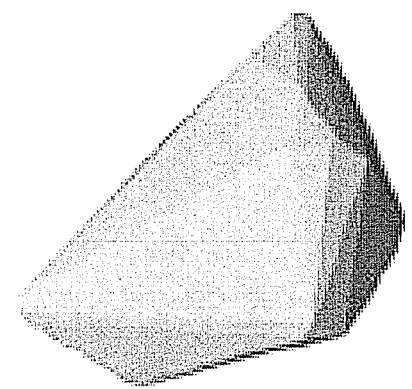
FIG. 4 illustrates alpha shape models obtained with different a values.
Figure 4:
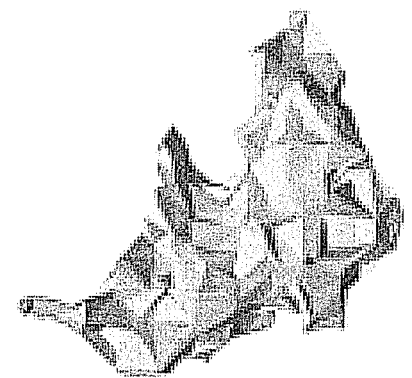
Figure 4:
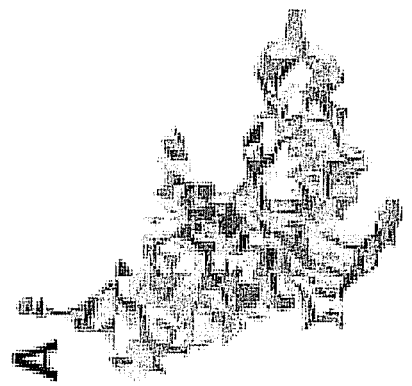

As illustrated in FIG. 4, the value of a controls the preciseness of the model of the object. FIG. 4 illustrates alpha shape models obtained with different alpha values. Smaller α values provide a more detailed representation of the molecular surface. However, as shown in element A, the molecular surface becomes fragmentary if the α value is too small as shown in element C, if the α value is too large, details of the surface can be lost. Element B shows a surface obtained with an optimal α value. Different α values can be tested to find the optimal alpha shape for the object. An optimal shape occurs when the alpha shape is a closed component. For example, to achieve an optimal shape, the α value can be between about 10 and about 20.

Figure 5:
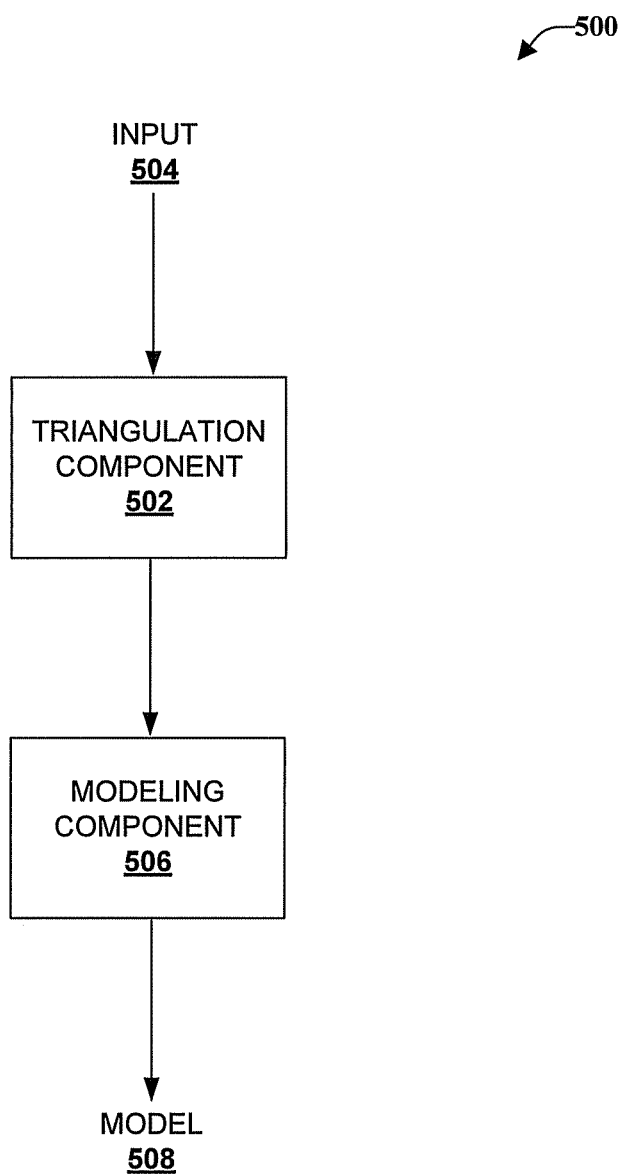
FIG. 5 is a schematic system block diagram of a system that models an object.

Referring now to FIG. 5, illustrated is a schematic system block diagram of a system 500 that models an object. The system 500 can include computer-executable components that can be stored in memory. One or more components of the system 500 can be executed by a processor.

The system can include a triangulation component 502. The triangulation component 502 can receive an input 504 regarding atom positions in an object (e.g., a biomolecule, biomolecular complex, or the like). The input 504 can be 3D information about the location of atoms in 3D space obtained through methods like X-ray crystallography or extracted from the Protein Data Bank (PDB) or other such databases.

The triangulation component 502 can construct a Delaunay triangulation based on the input 504. More specifically, the triangulation component 502 can take the atom positions of the input 504 as a set of P points in 3D space. The triangulation component 502 can construct the Delaunay triangulation for the set of P points. The Delaunay triangulation is a triangulation DT(P) such that no point P is inside a circumscribed sphere of any triangle of DT(P). The Delaunay triangulation of a set of points in d-dimensional spaces is the projection of the points of a convex hull onto a (d+1)-dimensional paraboloid.

The system can also include a model component 506 that can develop a model 508 of the object based on the Delaunay triangulation. The model 508 can be an alpha shape model. The model component can take the edges of the Delaunay triangulation constructed by the triangulation component 502 to provide the edges to construct an alpha shape. The alpha shape is a subset of the tetrahedrons in the Delaunay triangulation, which is a generalization of the convex hall of the point set of atom positions in 3D space.

The model component 506 can define the model 508 in the following manner. The model component 506 can define an alpha complex as the set of points S that is a sub-complex of the Delaunay triangulation. For a given value of α, the alpha complex includes all the simplexes in the Delaunay triangulation that have an empty circumsphere with a squared radius equal to, or smaller than, α. Here 'empty' means that the open sphere does not include any points of S. The alpha shape is then simply the domain covered by simplexes of the alpha complex. The alpha shape can be utilized as a model 508 for the object. Different α values can be tested to find the optimal alpha shape for the object.

Figure 6:
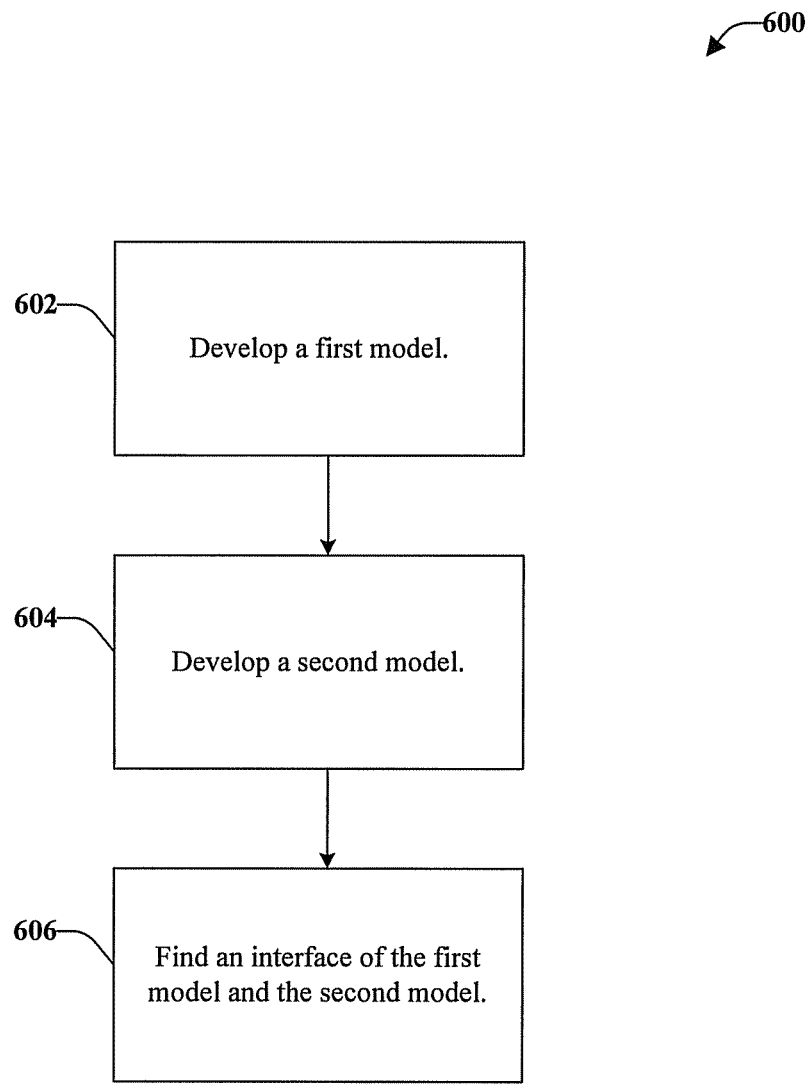
FIG. 6 is a schematic process flow diagram of a method for modeling an interface structure of an object.

Referring now to FIG. 6, illustrated is a schematic process flow diagram of a method 600 for modeling interface structure of an object. For simplicity of explanation, the method 600 can be an algorithm that is depicted and described as a series of acts. The acts can be one or more instructions stored in a memory that can be executed by a computer processor. The acts of method 600 can be stored on an article of manufacture to facilitate transporting and transferring method 600 to a computer. According to an embodiment, an article of manufacture can be a computer program accessible from any computer-readable device, carrier, or media. For example, the computer-readable medium can be any non-transitory computer-readable storage medium.

The object can be anything that can be represented by points with positions in 3D space. One such object is a biomolecule, such as a protein, a DNA molecule, a ligand, or the like. The object can also be a complex between biomolecules that can form between a protein and a protein, a protein and a DNA, a protein and a ligand, or a DNA and a ligand. The interface structure can be any interface between two objects. For example, the interface structure can be an interface between the two biomolecules in a complex between biomolecules. By way of example, a protein-DNA complex and an interface between the protein and the DNA in the protein-DNA complex are described with regard to method 600.

At element 602, a first model is developed. The first model can be based on the entire complex, like the protein-DNA complex. The first model can be developed according to the method of FIG. 1, in which information regarding at least two points corresponding to 3D positions of atoms in the complex is received as an input. A Delaunay triangulation can be constructed from the input. An alpha shape model of the complex can be constructed based on the Delaunay triangulation.

At element 604, a second model is developed. The second model can be based on a single molecule of the complex separate from the complex. For example, the second model can be a model of protein from the protein-DNA complex. The second model can be developed according to the method of FIG. 1, in which information regarding at least two points corresponding to 3D positions of atoms in the molecule (e.g., the protein molecule) can be received as an input. A Delaunay triangulation can be constructed from the input. An alpha shape model of the molecule can be constructed based on the Delaunay triangulation.

The method can also include developing a second model based on a molecule of the complex. The second stem can include receiving a second input of positions of two or more atoms in the molecule of the complex. Based on the second input, a second Delaunay triangulation can be constructed, and a second alpha shape can be constructed based on the second Delaunay triangulation. The method can include constructing the interface between the molecules in the complex as part of the second alpha shape. From the interface pattern, features can be computed and a classifier can be built for the prediction of molecular interactions (e.g., protein-DNA interactions, protein-ligand interactions, or the like).

At element 606, an interface model is developed. The interface model can be developed based on the first model of the complex and the second model of the molecule The α value for the first model and the α value for the second model are chosen so that the first model is a connected component and the second model is also a connected component. In this way, the interface model can be developed and/or constructed based on finding the interface between the two alpha shapes and extracting the interface surface.

According to an embodiment, the interface model can be developed at element 606 as follows. Interface atoms can be defined based on the first model of the complex and the second model of the molecule. Because the vertices of both first alpha shape model of the complex (e.g., with a complex surface of $A_i$) and the second alpha shape model of the molecule (e.g., with a complex surface of $B_i$) correspond to the surface atoms of the original structures, interface atoms can be defined as atoms residing in $B_i$ but not $A_i$.

Figure 7:
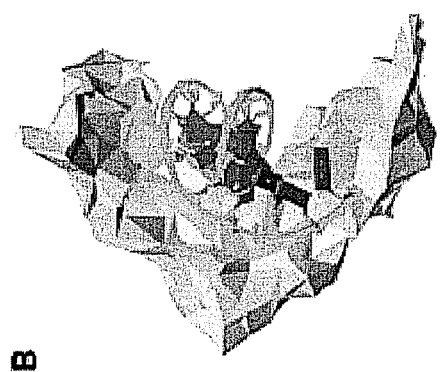
FIG. 7 illustrates examples of an interface of a protein-DNA complex obtained from an alpha shape model.
Figure 7:
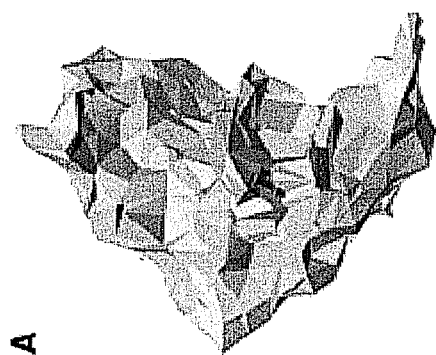

The interface model can be constructed using the interface atoms as part of the single molecule (e.g., protein) alpha shape developed at element 604. FIG. 7 is an illustration of a protein-DNA complex interface obtained from the alpha shape model. Element A of FIG. 7 shows the alpha shape model of the protein-DNA complex with the DNA structure inside. Element B of FIG. 7 shows the alpha shape model of the protein shown with the structure of the DNA chain. From the interface model, a number of features of the interface can be evaluated, such as the solid angle. These features of the interface can be used to build a classifier for the prediction of interactions, such as protein-DNA interactions, protein-ligand interactions, or the like.

Method 600 can be utilized to analyze interactions between biomolecules. The method 600 can be used in hardware or software executed by hardware for the modeling and analysis of biomolecules and for the prediction of biomolecular interactions. This modeling and analysis can be used in designing new drugs (ligands) and/or designing new proteins. Method 600 can be utilized in modeling and analyzing 3D point datasets other than biomolecules.

Method 600 is different from existing methods, which use distances among atoms. The distance features of existing methods are too simple and do not provide a high prediction power like method 600. Additionally, method 600 is 3D in nature and can be utilized to compute many statistical, topological, and geometric features that can provide high prediction power. Additionally, method 600 provides a fully automated algorithm to construct the interface surface between two biomolecules involved in an interaction (e.g., protein-protein interactions, protein-DNA interactions, protein-ligand interactions, and DNA-ligand interactions). Method 600 is not limited to biomolecular interactions, and can also be utilized for the modeling and analysis of the interface between two point patterns of any type.

Figure 8:
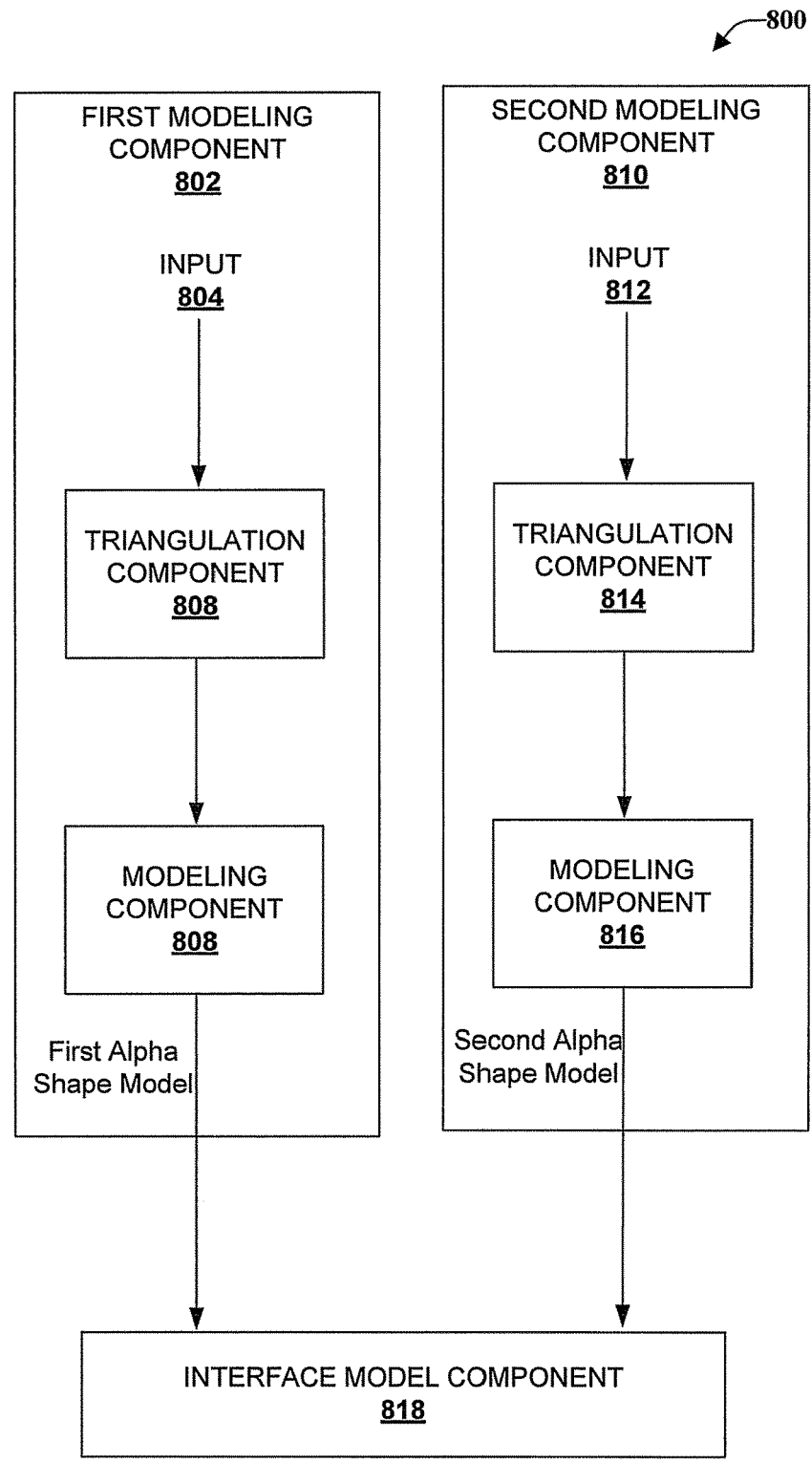
FIG. 8 is a schematic system block diagram of a system that models an interface structure of an object.

Referring now to FIG. 8, illustrated is a schematic system block diagram of a system 800 that models an interface structure of an object. The system 800 can include computer-executable components that can be stored in memory. One or more components of the system 800 can be executed by a processor.

The object can be anything that can be represented by points with positions in 3D space. One such object is a biomolecule, such as a protein, a DNA molecule, a ligand, or the like. The object can also be a complex between biomolecules that can form between a protein and a protein, a protein and a DNA, a protein and a ligand, or a DNA and a ligand. The interface structure can be any interface between two objects. For example, the interface structure can be an interface between the two biomolecules in a complex between biomolecules. By way of example, a protein-DNA complex and an interface between the protein and the DNA in the protein-DNA complex are described with regard to method 600.

System 800 includes a first model component 802 that develops a first model (e.g., alpha shape model) based on the entire object (e.g., a biomolecular complex between two biomolecules). The first model component 802 can include several sub-components. While each sub-component is illustrated as a separate sub-component, this illustration is merely for simplicity of explanation. It will be understood that one or more of the sub-components can be included in a single sub-component.

The first model component 802 can include a first input component 804, a first triangulation component 806 and a first modeling component 808. The sub-components can be utilized to construct a model of the entire complex, like a protein-DNA complex. The first input component 804 receives a first input including information regarding at least two points corresponding to 3D positions of atoms in the complex. The first triangulation component 806 can construct a Delaunay triangulation of the first input. The first modeling component 808 can construct an alpha shape model of the complex based on the Delaunay triangulation.

System 800 can also include a second model component 810 that develops a second model (e.g., alpha shape model based on a single component of the object (e.g., a biomolecule from the biomolecular complex between two biomolecules). The second model component 810 can include several sub-components. While each sub-component is illustrated as a separate sub-component, this illustration is merely for simplicity of explanation. It will be understood that one or more of the sub-components can be included in a single sub-component.

The second model component 810 can include a second input component 812, a second triangulation component 814 and a second modeling component 816. The sub-components can be utilized to construct a model of a component of the entire complex, like a protein from a protein-DNA complex. The second input component 812 receives a second input including information regarding at least two points corresponding to 3D positions of atoms in the component of the complex. The second triangulation component 814 can construct a Delaunay triangulation of the first input. The second modeling component 816 can construct an alpha shape model of the component of the complex based on the Delaunay triangulation.

System 800 can also include an interface model component 818 that can develop a model of the interface between the two components of the object. For example, the interface can be a protein-DNA interface of a protein-DNA complex caused due to protein-DNA interaction. The interface model component 816 can develop the interface model based on the alpha shape model of the complex created by the first modeling component 808 and the alpha shape model of the component of the complex created by the second modeling component 816. The first modeling component 808 and the second modeling component 816 can utilize α values so that the alpha models are connected components.

The interface model component 818 can take the advantage of the fact that the alpha model of the complex developed by first modeling component 808 and the alpha model of the component developed by the second modeling component 816 can each have vertices corresponding to atoms on the surface of either the complex (developed by the first modeling component 808) or the component (developed by the second modeling component 816). The interface model component 818 can define the interface by defining interface atoms that are in the alpha model of the component developed by the second modeling component 816), but not in the alpha model of the complex (developed by the first modeling component 808).

In this way, the interface model component 818 can develop and/or construct an alpha model of the interface surface based on finding the interface between the two objects and extracting the interface surface. From the interface model, a number of features of the interface can be evaluated, such as the solid angle. These features of the interface can be used to build a classifier for the prediction of interactions, such as protein-DNA interactions, protein-ligand interactions, or the like.

Figure 9:
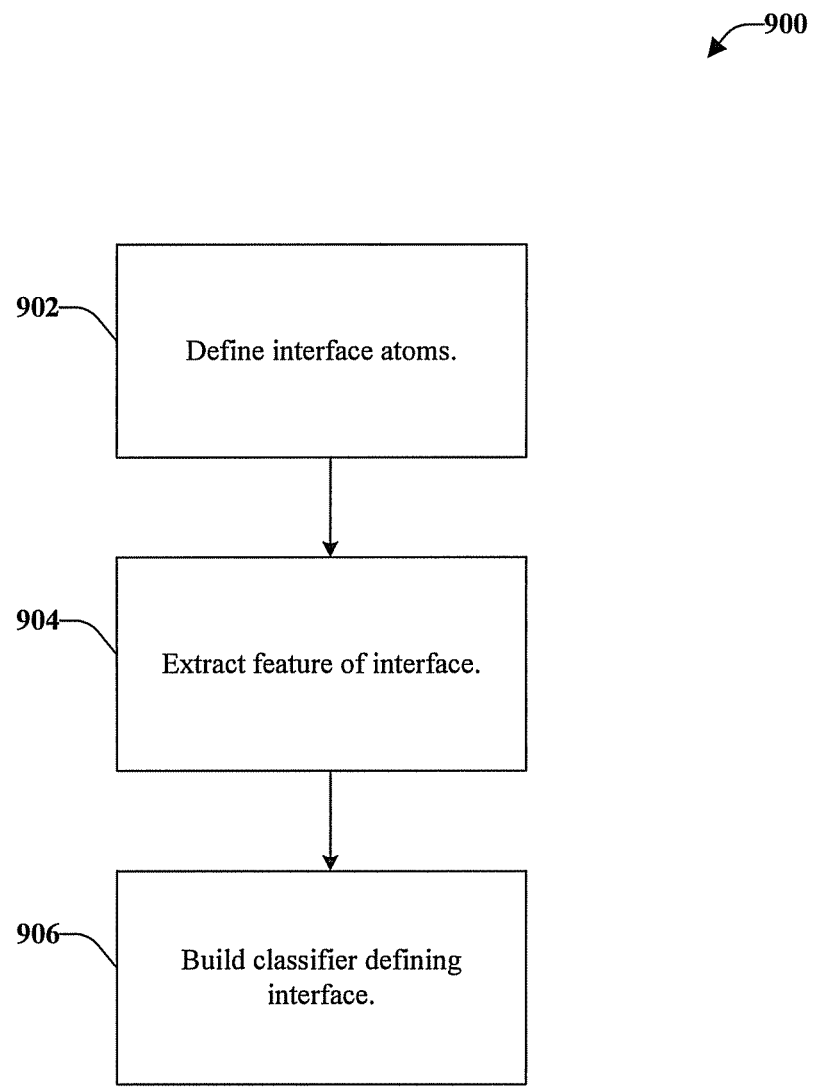
FIG. 9 is a schematic process flow diagram of a method for extracting features from an alpha shape model.

Referring now to FIG. 9, illustrated is a schematic process flow diagram of a method 900 for extracting features from an alpha shape model of an interface and classifying the interface. For simplicity of explanation, the method 900 can be an algorithm that is depicted and described as a series of acts. The acts can be one or more instructions stored in a memory that can be executed by a computer processor. The acts of method 900 can be stored on an article of manufacture to facilitate transporting and transferring method 900 to a computer. According to an embodiment, an article of manufacture can be a computer program accessible from any computer-readable device, carrier, or media. For example, the computer-readable medium can be any non-transitory computer-readable storage medium.

The method 900 can relate to an interface of an object. For example, the object can be a complex such as a biomolecular complex between protein and protein, protein and DNA, protein and ligand, or DNA and ligand. Described with respect to method 900 is a protein-DNA complex for simplicity of explanation.

At element 902, atoms of the protein-DNA interface are defined based on alpha shape models of the protein-DNA complex and the protein alone. The atoms of the interface can be defined by comparing atoms on the surface the alpha shape model of the protein-DNA complex and the surface of the alpha shape model of the protein alone. Atoms that are on the surface of the alpha shape model of the protein alone but not on the surface of the alpha shape model of the protein-DNA complex can be defined as atoms of the protein-DNA interface.

At element 904, features of the protein-DNA interface can be extracted, including statistical, topological, and geometric features of the interface. The features that can be extracted can include atom type, residue type, surface curvature, solid angle, and the like. All 20 amino acid residue types can be considered. According to the significance of atom types in the protein-DNA structure, 36 special atom types can be considered, as shown in TABLE I, for use in an interface-atom curvature dependent discriminatory function.

TABLE I

List of atom types utilized in the interface-atom curvature dependent discriminatory function.

| C | $C_\alpha$ | $C_\beta$ | $C_\delta$ | $C_{\delta 1}$ | $C_{\delta 2}$ |
|---|---|---|---|---|---|
| $C_\epsilon$ | $C_{\epsilon 1}$ | $C_{\epsilon 2}$ | $C_{\epsilon 3}$ | $C_\gamma$ | $C_{\gamma 1}$ |
| $C_{\gamma 2}$ | $CH_2$ | $C_\zeta$ | $C_{\zeta 1}$ | $C_{\zeta 2}$ | N |
| $N_{\delta 1}$ | $N_{\delta 2}$ | $N_\epsilon$ | $N_{\epsilon 1}$ | $N_{\epsilon 2}$ | $NH_1$ |
| $NH_2$ | $N_\zeta$ | O | $O_{\delta 1}$ | $O_{\delta 2}$ | $O_{\epsilon 1}$ |
| $O_{\epsilon 2}$ | $O_\gamma$ | $O_{\gamma 1}$ | OH | $S_\delta$ | $S_\gamma$ |

The interface surface curvature can be represented by the solid angle of the interface atoms in the alpha shape model. The solid angle is defined as follows: let OABC be the vertices of a tetrahedron with an origin at O subtended by the triangular face of ABC. Let $\Phi_{AB}$ be the dihedral angle between the planes that contain the tetrahedral faces OAC and OBC. Define $\Phi_{BC}$ and $\Phi_{AC}$ similarly. The solid angle at O subtended by the triangular surface ABC is given by EQUATION (1). The solid angle of an interface atom is transformed to the range of −1 (cleft) to 1 (knob) using $\cos(\Omega/4)$.

$$\Omega = \Phi_{AB} + \Phi_{BC} + \Phi_{AC} - \pi \tag{1}$$

At element 906, a classifier that can classify the interface is built according to the features. The classifier can be used for the prediction of biomolecular interactions. For example, the classifier can define biomolecules as two different types: those that interact and those that do not interact.

For example, the classifier can be formed according to conditional probability. A discriminatory function of whether the biomolecules interact or do not interact can be determined (e.g., based on the geometric, statistical, and/or topological features of the interface). The discriminatory function can be a curvature dependent function.

With regard to conditional probability, all possible protein-DNA structures can be divided into two sets: C for the correct structures (native structures) and I for the incorrect structures (decoy structures). A set of properties can be established for which the correct structures and incorrect structures are distinctly different. Properties can include molecular flexibility, electrostatic strength, interatomic distance, or the like. The interface surface curvature of the protein-DNA structure is considered by using a set of features, including solid angle of interface atom i (Si), residue type (ri) and atom type (ai), [{Si, ri, ai}], to characterize the protein-DNA interface. A scoring function the structure is in the correct set when given that it has a set of features [{Si, ri, ai}] can be expressed through conditional probability, an assumption that all the solid angles are independent of one another and the correlations of a structure can be expressed by the joint probability of the correctness of every interface atom curvature, and the Bayesian theorem as:

$$S = -\sum_i \ln \frac{P_c((Sa_i, r_i, a_i) \mid C)}{P((Sa_i, r_i, a_i))} \tag{2}$$

Based on the scoring function, a classification library can be created. The classification library can indicate, for example, whether two biomolecules will interact based on the interface and/or the characteristics of the interface. An initial template library can be set up, containing known protein-DNA complexes. The template library can be used to compare the target structure and the structures in the library. The target structure can be scanned against the template structures in the library for similar protein structure. The largest scored template structure can be selected. A new structure can be created by replacing the protein sequence of the template structure with the aligned target structure. The new structure can be scored using the scoring function of EQUATION (2) of the curvature dependent method.

Figure 10:
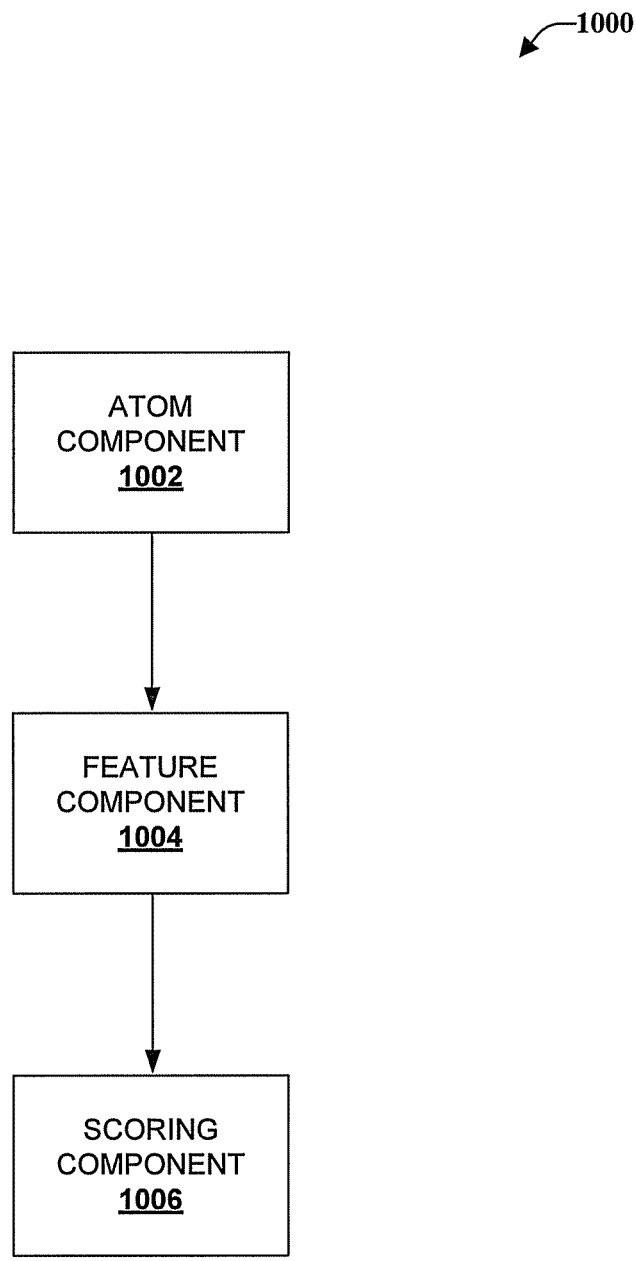
FIG. 10 is a schematic system block diagram of a system that extracts features from an alpha shape model.

Referring now to FIG. 10, illustrated is a schematic system block diagram of a system 1000 that extracts features from an alpha shape model of an interface and classifies the interface. The system 1000 can include computer-executable components that can be stored in memory. One or more components of the system 1000 can be executed by a processor.

The system 1000 can facilitate extraction of features from an interface of an object. For example, the object can be a complex such as a biomolecular complex between protein and protein, protein and DNA, protein and ligand, or DNA and ligand. Described with respect to system 1000 is a protein-DNA complex for simplicity of explanation.

System 1000 can include an atom definition component 1002 that can define atoms of the protein-DNA interface based on alpha shape models of the protein-DNA complex and the protein alone. The atom definition component 1002 can define the atoms of the interface by comparing atoms on the surface the alpha shape model of the protein-DNA complex and the surface of the alpha shape model of the protein alone. Atoms that are on the surface of the alpha shape model of the protein alone but not on the surface of the alpha shape model of the protein-DNA complex can be defined as atoms of the protein-DNA interface.

System 1000 can also include a feature component 1004 the can extract features of the protein-DNA interface from the interface atoms defined by the atom definition component 1002. The features that can be extracted by the feature component 1004 can include atom type, residue type, surface curvature, solid angle, and the like.

Based on the features extracted by the feature component 1004, a scoring component 1006 can consult a classification library and determine whether a ligand or DNA will bind to a protein. For example, the scoring component 1006 can employ EQUATION (2) to make the determination. This determination can aid, for example, in the development of new drugs that can be ligands to certain proteins.

The systems and methods described above can be especially useful for modeling and analysis of biomolecular interactions. The study of biomolecular interactions has important applications to drug design. For example, if a drug molecule is a ligand that can interact with or dock to a protein, it may be able to prevent the protein from functioning properly and, thus, stop a disease-causing process. Traditional methods of determining whether a ligand will dock to a given protein, such as biological experiments, are time consuming and costly. The systems and methods described herein can determine whether a ligand will dock to a given protein in an efficient and cost-effective manner through modeling the interface surface between the protein and ligand.

Although the systems and methods can be utilized with biomolecules, use of the systems and methods described above is not limited to biomolecules. It can be applied to any patterns containing two sets of points or more in three-dimensional, or higher, space. Any interface can be modeled and analyzed. Positions of the points can be taken as input and the interface surface and its features can be automatically computed. Features of the interface can be used to design pattern classifiers for prediction of interaction.

Figure 11:
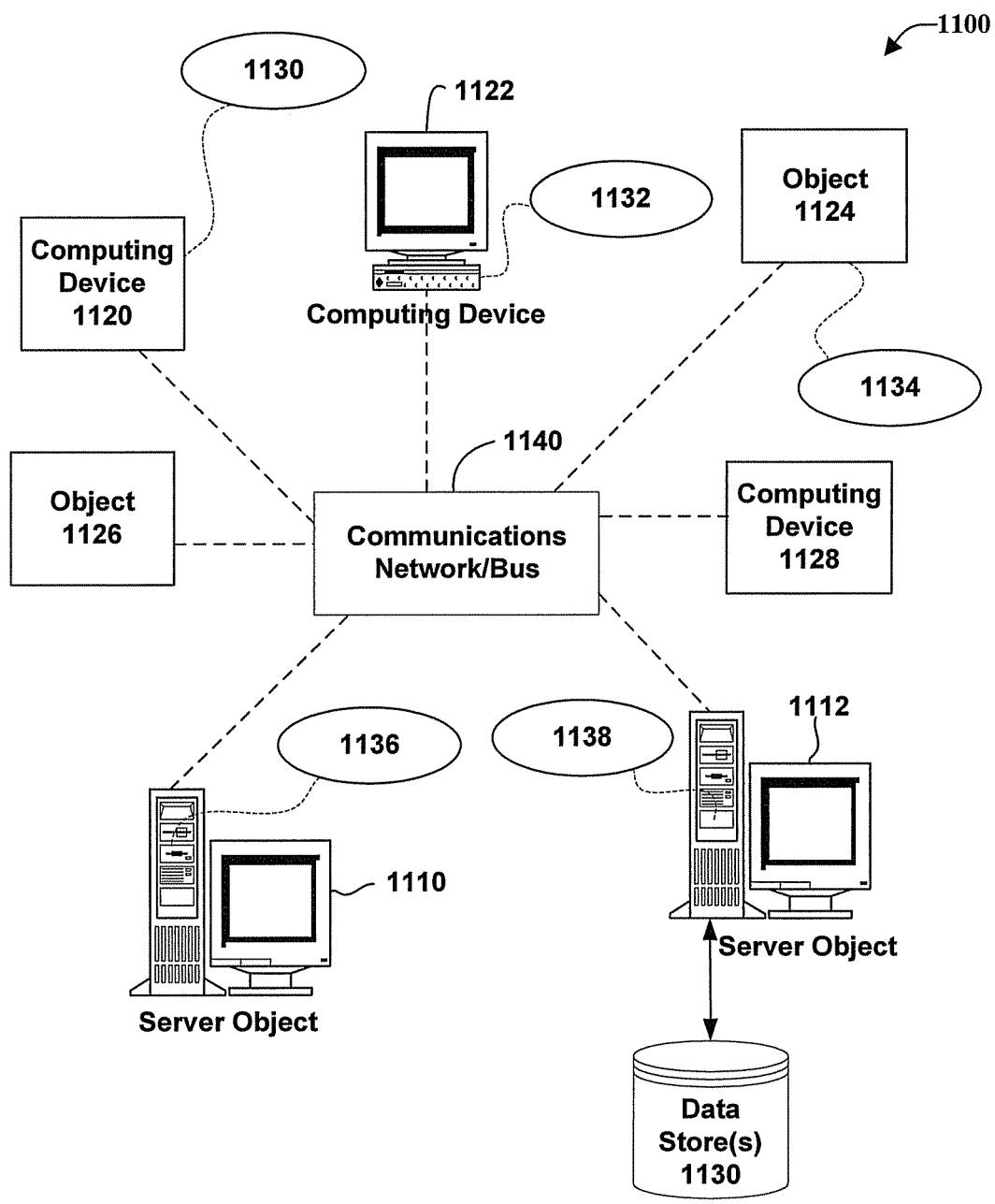
FIG. 11 illustrates an exemplary computer network in which various embodiments described herein can be implemented.
Figure 12:
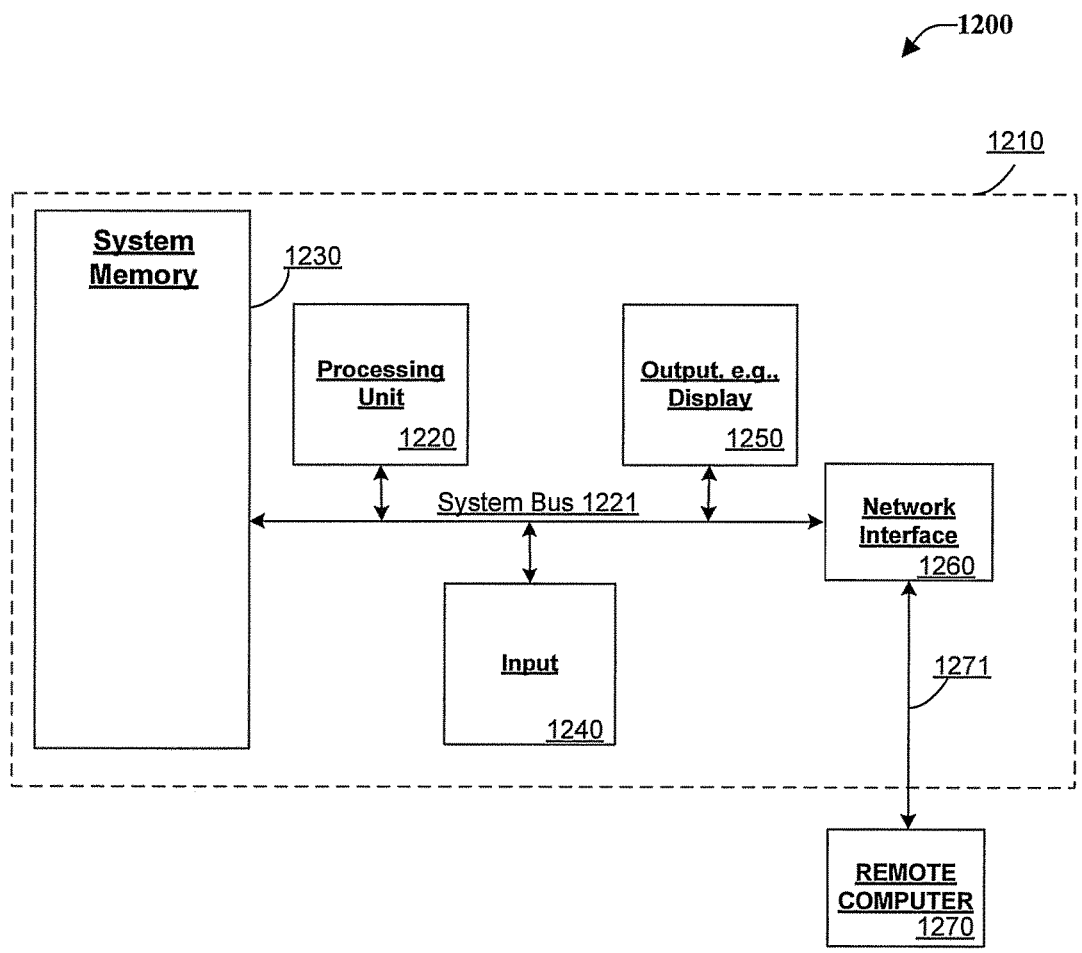
FIG. 12 illustrates an exemplary computing environment in which the various embodiments described herein can be implemented.

The systems and methods described above can be implemented in software, hardware, or a combination thereof FIGS. 11 and 12 provide hardware context for the systems and methods described above. FIG. 11 illustrates a non-limiting example of a computing network 1100 that can be utilized in connection with facilitating the systems and methods described above. FIG. 12 illustrates a non-limiting example of a computing environment 1200 that can be utilized in connection with facilitating the systems and method described above. It should be appreciated that artificial intelligence can also be utilized to implement the systems and methods described herein.

Referring now to FIG. 11, illustrated is a schematic diagram of an exemplary networked or distributed computing environment 1100. The distributed computing environment comprises computing objects 1110, 1112, etc. and computing objects or devices 1120, 1122, 1124, 1126, 1128, etc., which can include programs, methods, data stores, programmable logic, etc., as represented by applications 1130, 1132, 1134, 1136, 1138. It can be appreciated that objects 1110, 1112, etc. and computing objects or devices 1120, 1122, 1124, 1126, 1128, etc. can comprise different devices, such as remote controllers, PDAs, audio/video devices, mobile phones, MP3 players, laptops, etc.

Each object 1110, 1112, etc. and computing objects or devices 1120, 1122, 1124, 1126, 1128, etc. can communicate with one or more other objects 1110, 1112, etc. and computing objects or devices 1120, 1122, 1124, 1126, 1128, etc. by way of the communications network 1140, either directly or indirectly. Even though illustrated as a single element in FIG. 11, network 1140 can comprise other computing objects and computing devices that provide services to the system of FIG. 11, and/or can represent multiple interconnected networks, which are not shown. Each object 1110, 1112, etc. or 1120, 1122, 1124, 1126, 1128, etc. can also contain an application, such as applications 1130, 1132, 1134, 1136, 1138, that might make use of an API, or other object, software, firmware and/or hardware, suitable for communication with or implementation of the delayed interaction model as provided in accordance with various embodiments.

There are a variety of systems, components, and network configurations that support distributed computing environments. For example, computing systems can be connected together by wired or wireless systems, by local networks or widely distributed networks. Currently, many networks are coupled to the Internet, which provides an infrastructure for widely distributed computing and encompasses many different networks, though any network infrastructure can be used for exemplary communications made incident to the techniques as described in various embodiments.

Thus, a host of network topologies and network infrastructures, such as client/server, peer-to-peer, or hybrid architectures, can be utilized. In a client/server architecture, particularly a networked system, a client is usually a computer that accesses shared network resources provided by another computer, e.g., a server. In the illustration of FIG. 11, as a non-limiting example, computers 1120, 1122, 1124, 1126, 1128, etc. can be thought of as clients and computers 1110, 1112, etc. can be thought of as servers where servers 1110, 1112, etc. provide data services, such as receiving data from client computers 1120, 1122, 1124, 1126, 1128, etc., storing of data, processing of data, transmitting data to client computers 1120, 1122, 1124, 1126, 1128, etc., although any computer can be considered a client, a server, or both, depending on the circumstances. Any of these computing devices can be processing data, or requesting services or tasks that can implicate the delayed interaction model and related techniques as described herein for one or more embodiments.

A server is typically a remote computer system accessible over a remote or local network, such as the Internet or wireless network infrastructures. The client process can be active in a first computer system, and the server process can be active in a second computer system, communicating with one another over a communications medium, thus providing distributed functionality and allowing multiple clients to take advantage of the information-gathering capabilities of the server. Any software objects utilized pursuant to the direction based services can be provided standalone, or distributed across multiple computing devices or objects.

In a network environment in which the communications network/bus 1140 is the Internet, for example, the servers 1110, 1112, etc. can be Web servers with which the clients 1120, 1122, 1124, 1126, 1128, etc. communicate via any of a number of known protocols, such as the hypertext transfer protocol (HTTP). Servers 1110, 1112, etc. can also serve as clients 1120, 1122, 1124, 1126, 1128, etc., as can be characteristic of a distributed computing environment.

As a further non-limiting example, various embodiments described herein apply to any handheld, portable and other computing devices and computing objects of all kinds are contemplated for use in connection with the various embodiments described herein, i.e., anywhere that a device can request pointing based services. Accordingly, the general purpose remote computer described below in FIG. 12 is but one example, and the embodiments of the subject disclosure can be implemented with any client having network/bus interoperability and interaction.

Although not required, any of the embodiments can partly be implemented via an operating system, for use by a developer of services for a device or object, and/or included within application software that operates in connection with the operable component(s). Software can be described in the general context of computer executable instructions, such as program modules, being executed by one or more computers, such as client workstations, servers or other devices. Those skilled in the art will appreciate that network interactions can be practiced with a variety of computer system configurations and protocols.

FIG. 12 illustrates an example of a suitable computing system environment 1200 in which one or more of the embodiments can be implemented, although as made clear above, the computing system environment 1200 is only one example of a suitable computing environment and is not intended to suggest any limitation as to the scope of use or functionality of any of the embodiments. Neither should the computing environment 1200 be interpreted as having any dependency or requirement relating to any one or combination of components illustrated in the exemplary operating environment 1200.

With reference to FIG. 12, an exemplary remote device for implementing one or more embodiments herein can include a general purpose computing device in the form of a handheld computer 1210. Components of handheld computer 1210 can include, but are not limited to, a processing unit 1220, a system memory 1230, and a system bus 1221 that couples various system components including the system memory to the processing unit 1220.

Computer 1210 typically includes a variety of computer readable media and can be any available media that can be accessed by computer 1210. The system memory 1230 can include computer storage media in the form of volatile and/or nonvolatile memory such as read only memory (ROM) and/or random access memory (RAM). By way of example, and not limitation, memory 1230 can also include an operating system, application programs, other program modules, and program data.

A user can enter commands and information into the computer 1210 through input devices 1240. A monitor or other type of display device is also connected to the system bus 1221 via an interface, such as output interface 1250. In addition to a monitor, computers can also include other peripheral output devices such as speakers and a printer, which can be connected through output interface 1250.

The computer 1210 can operate in a networked or distributed environment using logical connections to one or more other remote computers, such as remote computer 1270. The remote computer 1270 can be a personal computer, a server, a router, a network PC, a peer device or other common network node, or any other remote media consumption or transmission device, and can include any or all of the elements described above relative to the computer 1210. The logical connections depicted in FIG. 12 include a network 1271, such local area network (LAN) or a wide area network (WAN), but can also include other networks/buses. Such networking environments are commonplace in homes, offices, enterprise-wide computer networks, intranets and the Internet.

With respect to any figure or numerical range for a given characteristic, a figure or a parameter from one range may be combined with another figure or a parameter from a different range for the same characteristic to generate a numerical range.

Other than the operating examples, or where otherwise indicated, all numbers, values, and/or expressions referring to quantities of ingredients, reaction conditions, etc., used in the specification and claims are to be understood as modified in all instances by the term "about."

The embodiments as disclosed and described in the application are intended to be illustrative and explanatory, and not limiting. Modifications and variations of the disclosed embodiments, for example, of the processes and apparatuses employed (or to be employed) as well as of the compositions and treatments used (or to be used), are possible; all such modifications and variations are intended to be within the scope of this application.

What has been described above includes examples of the subject innovation. It is, of course, not possible to describe every conceivable combination of components or methods for the purpose of describing the subject innovation. One having ordinary skill in the art, however, can recognize that many further combinations and permutations of the disclosed information are possible. Accordingly, the disclosed information is intended to embrace all such modifications, alterations and variations that fall within the spirit and scope of the applications and the appended claims.

Furthermore, to the extent that the term "includes," "has," "involves," or variants thereof are used either in the detailed description or the claims, such terms are intended to be inclusive in a manner similar to the term "comprising" as "comprising" is interpreted when employed as a transitional word in a claim.

What is claimed is:

1. A method, comprising:
   generating, by a system comprising a processor, a first three-dimensional model of a complex, wherein the complex comprises a first molecule and a second molecule, and wherein the first-three dimensional model comprises a first alpha shape;
   identifying, by the system, a first set of atoms located on a surface of the first alpha shape, wherein the surface of the first alpha shape corresponds to at least a first portion of a first surface of the first molecule and at least a second portion of a second surface of the second molecule;
   generating, by the system, a second three-dimensional model of the first molecule, wherein the second three-dimensional model comprises a second alpha shape;
   identifying, by the system, a second set of atoms located on a surface of the second alpha shape, wherein the surface of the second alpha shape includes at least the first portion of the first surface of the first molecule;
   determining, by the system, a third set of atoms included in the second set of atoms and not included in the first set of atoms; and
   generating, by the system, a third three-dimensional model of a binding interface between the first molecule and the second molecule in the complex based on the second alpha shape and the third set of atoms, wherein the third three-dimensional model comprises the third set of atoms.

2. The method of claim 1, further comprising:
   determining, by the system, one or more features of the binding interface based on the third three-dimensional model, including determining solid angles between respective atoms of the third set of atoms.

3. The method of claim 1, further comprising choosing, by the system, an alpha value resulting in the second alpha shape being a connected component.

4. The method of claim 2, wherein the determining the one or more features further comprises determining types of respective atoms in the third set of atoms, and types of residues of the respective atoms.

5. The method of claim 2, wherein the determining the one or more features further comprises determining a statistical feature of the binding interface.

6. The method of claim 2, wherein the determining the one or more features further comprises determining a topological feature of the binding interface.

7. The method of claim 2, wherein the determining the one or more features further comprises determining a geometric feature of the binding interface.

8. The method of claim 2, wherein the determining the one or more features further comprises determining a surface curvature of the binding interface.

9. The method of claim 2, further comprising:
   scoring, by the system, the binding interface according to a discriminatory scoring function based on the one or more features; and
   determining, by the system, whether the first molecule is configured to bind with the second molecule based on the scoring.

10. The method of claim 1, wherein the generating the first three-dimensional model comprises:
    receiving first information identifying positions of first atoms included in the complex relative to a three-dimensional space;
    generating a first Delaunay triangulation based on the positions of the first atoms, wherein the first Delaunay triangulation comprises a first set of tetrahedrons; and
    generating the first alpha shape using a subset of the first tetrahedrons corresponding to edges of the first Delaunay triangulation.

11. The method of claim 10, wherein the generating the second three-dimensional model comprises:
    receiving second information identifying positions of second atoms included in the first molecule relative to the three-dimensional space;
    generating the second Delaunay triangulation based on the positions of the second atoms, wherein the second Delaunay triangulation comprises a second set of tetrahedrons; and
    generating the second alpha shape using a subset of the second tetrahedrons corresponding to edges of the second Delaunay triangulation.

12. The method of claim 9, further comprising:
    based on a determination that the first molecule is configured to bind with the second molecule, providing, by the system, information for the complex in a classification library database that identifies characteristics of binding interfaces of respective molecules of known molecular complexes, the information identifying the first molecule and the second molecule as a bound molecular complex and identifying the one or more features of the binding interface.

13. The method of claim 12, further comprising:
employing, by the system, the classification library to determine whether a third molecule will bind with one or more molecules included in the classification library, including the first molecule and the second molecule.

14. A non-transitory computer readable storage medium having stored thereon computer executable instructions that, in response to execution, cause a system including a processor to perform operations, the operations comprising:
generating a first three-dimensional alpha shape corresponding to a complex comprising a first molecule and a second molecule;
identifying a first set of atoms located on a first surface of the first three-dimensional alpha shape;
generating a second three-dimensional alpha shape corresponding to the first molecule, wherein a portion of the first surface of the first three-dimensional alpha shape includes a first portion of a second surface of the second three-dimensional alpha shape;
determining a second set of atoms located on a second portion of the second surface of the second three-dimensional alpha shape and not included in the first set of atoms; and
generating a third three-dimensional alpha shape of a binding interface between the first molecule and the second molecule in the complex based on the second three-dimensional alpha shape and the second set of atoms, wherein the third three-dimensional alpha shape comprises the second set of atoms.

15. The non-transitory computer readable storage medium of claim 14, wherein the first molecule is a biomolecule and the second molecule is a protein.

16. The non-transitory computer readable storage medium of claim 14, wherein the operations further comprise:
determining one or more features of the binding interface based on the third three-dimensional alpha shape including determining solid angles between respective atoms of the second set of atoms.

17. The non-transitory computer readable storage medium of claim 16, wherein the operations further comprise:
scoring the binding interface surface according to a discriminatory scoring function based on the one or more features; and
determining whether the first molecule is configured to bind with the second molecule based on the scoring.

18. A system, comprising:
a memory that stores computer-executable instructions; and
a processor that facilitates execution of the computer-executable instructions to at least:
create a first three-dimensional alpha shape model of a complex between a biomolecule and a protein;
identify a first set of atoms located on a surface of the first three-dimensional alpha shape model;
create a second three-dimensional alpha shape model of the biomolecule;
determine a second set of atoms located on a surface of the second three-dimensional alpha shape that are not included in the first set of atoms; and
generate a third three-dimensional alpha shape of a binding interface between the biomolecule and the protein within the complex based on the second set of atoms and the second three-dimensional alpha shape, wherein the third three-dimensional alpha shape model comprises the second set of atoms.

19. The system of claim 18, wherein the processor further facilitates execution of the computer-executable instructions to:
determine one or more features of the binding interface based on the third three-dimensional alpha shape, including solid angles between respective atoms of the second set of atoms.

20. The system of claim 19, wherein the processor further facilitates execution of the computer-executable instructions to:
score the binding interface surface according to a discriminatory scoring function based on the one or more features; and
determine whether the biomolecule is configured to bind with the protein based on the score.

21. The system of claim 19, wherein the one or more features further comprises types of respective atoms in the second set of atoms, and types of residues of the respective atoms.

22. The system of claim 18, wherein the processor further facilitates execution of the computer-executable instructions to select an alpha value that results in the second three-dimensional alpha shape model being a closed component.

* * * * *